United States Patent
Booth

(10) Patent No.: US 11,733,196 B2
(45) Date of Patent: *Aug. 22, 2023

(54) SYSTEM AND METHOD FOR OPTIMIZING INSULIN DOSAGES FOR DIABETIC SUBJECTS

(71) Applicant: Aseko, Inc., Greenville, SC (US)

(72) Inventor: Robert C. Booth, Columbus, NC (US)

(73) Assignee: Aseko, Inc., Greenville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/474,001

(22) Filed: Sep. 13, 2021

(65) Prior Publication Data

US 2022/0074883 A1 Mar. 10, 2022

Related U.S. Application Data

(63) Continuation of application No. 15/862,819, filed on Jan. 5, 2018, now Pat. No. 11,131,643, which is a continuation of application No. 13/610,287, filed on Sep. 11, 2012, now Pat. No. 9,897,565.

(51) Int. Cl.
  *G01N 27/327* (2006.01)
  *A61B 5/145* (2006.01)
  *G16H 40/63* (2018.01)
  *G16H 40/67* (2018.01)
  *G16H 10/60* (2018.01)
  *G16H 20/17* (2018.01)
  *G16H 10/40* (2018.01)

(52) U.S. Cl.
  CPC ..... *G01N 27/3271* (2013.01); *A61B 5/14532* (2013.01); *G16H 10/40* (2018.01); *G16H 10/60* (2018.01); *G16H 20/17* (2018.01); *G16H 40/63* (2018.01); *G16H 40/67* (2018.01)

(58) Field of Classification Search
  None
  See application file for complete search history.

(56) References Cited

U.S. PATENT DOCUMENTS

| | | | |
|---|---|---|---|
| 4,055,175 A | 10/1977 | Clemens et al. | |
| 4,151,845 A | 5/1979 | Clemens | |
| 4,206,755 A | 6/1980 | Klein | |
| 4,464,170 A | 8/1984 | Clemens et al. | |
| 4,850,959 A | 7/1989 | Findl | |
| 5,091,190 A | 2/1992 | Kuczynski et al. | |
| 5,614,224 A | 3/1997 | Womack | |
| 5,998,363 A | 12/1999 | Forse et al. | |
| 6,428,825 B2 | 8/2002 | Sharma et al. | |
| 6,472,366 B2 | 10/2002 | Kishino et al. | |
| 6,572,542 B1 | 6/2003 | Houben et al. | |
| 6,605,039 B2 | 8/2003 | Houben et al. | |
| 6,615,081 B1 | 9/2003 | Boveja | |
| 6,808,703 B2 | 10/2004 | Park et al. | |
| 6,890,568 B2 | 5/2005 | Pierce et al. | |
| 6,927,246 B2 | 8/2005 | Noronha et al. | |
| 7,498,318 B1 | 3/2009 | Stahl et al. | |
| 7,704,226 B2 | 4/2010 | Mueller, Jr. et al. | |
| 7,824,333 B2 | 11/2010 | Otto et al. | |
| 7,837,622 B2 | 11/2010 | Itoh et al. | |
| 7,985,848 B2 | 7/2011 | Woo et al. | |
| 8,088,731 B2 | 1/2012 | Knudsen et al. | |
| 8,117,020 B2 | 2/2012 | Abensour et al. | |
| 8,185,412 B1 | 5/2012 | Harpale | |
| 8,198,320 B2 | 6/2012 | Liang et al. | |
| 8,204,729 B2 | 6/2012 | Sher | |
| 8,257,735 B2 | 9/2012 | Lau et al. | |
| 8,318,221 B2 | 11/2012 | Miller et al. | |
| 8,329,232 B2 | 12/2012 | Cheng et al. | |
| 8,333,752 B2 | 12/2012 | Veit et al. | |
| 8,370,077 B2 | 2/2013 | Bashan et al. | |
| 8,420,125 B2 | 4/2013 | Webster et al. | |
| 8,420,621 B2 | 4/2013 | Lai et al. | |
| 8,457,901 B2 | 6/2013 | Beshan et al. | |
| 8,527,208 B2 | 9/2013 | Prud'homme et al. | |
| 8,548,544 B2 | 10/2013 | Kircher, Jr. et al. | |
| 8,571,801 B2 | 10/2013 | Anfinsen et al. | |

(Continued)

FOREIGN PATENT DOCUMENTS

EP 461207 A1 12/1991
EP 483595 A2 5/1992

(Continued)

OTHER PUBLICATIONS

Kaufman et al. (Diabetes Metab. Res. Rev., 1999, vol. 15, p. 338-352). (Year: 1999).*

*Primary Examiner* — Pablo S Whaley

(74) *Attorney, Agent, or Firm* — Honigman LLP; Brett A. Krueger

(57) ABSTRACT

A method and system for optimizing insulin dosages for diabetic subjects which includes a processor for calculating basal and bolus dosages to be recommended for meal types including breakfast, lunch, dinner, snack, or at miscellaneous times. The bolus calculations are specifically directed to time periods which are taken from either pre-meal, post-meal, bedtime, mid-sleep or miscellaneous times. The processor calculates an optimized bolus for a specific time period and meal type based upon prior basal dosages, prior glucose doses, hypoglycemia thresholds, mid-point of target ranges, and subject insulin sensitivity factors. A display is provided to the subject for sensing the optimized insulin dosage recommended at a specific time period and for a specific meal type.

27 Claims, 7 Drawing Sheets

(56) References Cited

U.S. PATENT DOCUMENTS

| | | |
|---|---|---|
| 8,579,879 B2 | 11/2013 | Palerm et al. |
| 8,600,682 B2 | 12/2013 | Bashan et al. |
| 8,635,054 B2 | 1/2014 | Brown |
| 8,679,016 B2 | 3/2014 | Mastrototaro et al. |
| 8,690,934 B2 | 4/2014 | Boyden et al. |
| 8,700,161 B2 | 4/2014 | Harel et al. |
| 8,703,183 B2 | 4/2014 | Lara |
| 8,718,949 B2 | 5/2014 | Blomquist et al. |
| 8,755,938 B2 | 6/2014 | Weinert et al. |
| 8,766,803 B2 | 7/2014 | Bousamra et al. |
| 8,828,390 B2 | 9/2014 | Herrera et al. |
| 8,834,367 B2 | 9/2014 | Laan et al. |
| 8,870,807 B2 | 10/2014 | Mantri et al. |
| 8,911,367 B2 | 12/2014 | Brister et al. |
| 8,919,180 B2 | 12/2014 | Gottlieb et al. |
| 8,954,373 B2 | 2/2015 | Atlas et al. |
| 8,992,464 B2 | 3/2015 | Bashan et al. |
| 2001/0002269 A1 | 5/2001 | Zhao |
| 2003/0028089 A1* | 2/2003 | Galley ............... A61P 3/10 128/920 |
| 2003/0199445 A1 | 10/2003 | Knudsen et al. |
| 2003/0208110 A1 | 11/2003 | Mault et al. |
| 2003/0208113 A1 | 11/2003 | Mault et al. |
| 2005/0020681 A1 | 1/2005 | Takayama et al. |
| 2005/0054818 A1 | 3/2005 | Brader et al. |
| 2005/0096637 A1 | 5/2005 | Heruth |
| 2005/0176621 A1 | 8/2005 | Brader et al. |
| 2005/0197621 A1 | 9/2005 | Poulsen et al. |
| 2005/0267195 A1 | 12/2005 | Mikoshiba et al. |
| 2006/0040003 A1 | 2/2006 | Needleman et al. |
| 2006/0078593 A1 | 4/2006 | Strozier et al. |
| 2006/0188995 A1 | 8/2006 | Ryan et al. |
| 2007/0036872 A1 | 2/2007 | Tsuboi et al. |
| 2007/0060796 A1 | 3/2007 | Kim |
| 2007/0160678 A1 | 7/2007 | Guimberteau et al. |
| 2007/0249916 A1 | 10/2007 | Pesach et al. |
| 2007/0282186 A1 | 12/2007 | Gilmore |
| 2008/0119421 A1 | 5/2008 | Tuszynski et al. |
| 2008/0139511 A1 | 6/2008 | Friesen |
| 2008/0299079 A1 | 12/2008 | Meezan et al. |
| 2009/0029933 A1 | 1/2009 | Velloso et al. |
| 2009/0099438 A1 | 4/2009 | Flanders |
| 2009/0110752 A1 | 4/2009 | Shang et al. |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0242399 A1 | 10/2009 | Kamath et al. |
| 2009/0312250 A1 | 12/2009 | Ryu et al. |
| 2010/0121170 A1 | 5/2010 | Rule |
| 2010/0286601 A1 | 11/2010 | Yodfat et al. |
| 2011/0021894 A1 | 1/2011 | Mohanty et al. |
| 2011/0071365 A1 | 3/2011 | Lee et al. |
| 2011/0098548 A1 | 4/2011 | Budiman et al. |
| 2011/0115894 A1 | 5/2011 | Burnett |
| 2011/0119081 A1 | 5/2011 | Vespasiani |
| 2011/0173308 A1 | 7/2011 | Gutekunst |
| 2011/0178008 A1 | 7/2011 | Arai et al. |
| 2011/0217396 A1 | 9/2011 | Oldani |
| 2011/0229602 A1 | 9/2011 | Aymard et al. |
| 2011/0286984 A1 | 11/2011 | Huang |
| 2011/0305771 A1 | 12/2011 | Sampalis |
| 2012/0003339 A1 | 1/2012 | Minacapelli |
| 2012/0053222 A1 | 3/2012 | Gorrell et al. |
| 2012/0058942 A1 | 3/2012 | Dupre |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0244096 A1 | 9/2012 | Xie et al. |
| 2012/0295985 A1 | 11/2012 | Miller et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0190583 A1 | 7/2013 | Grosman et al. |
| 2013/0217990 A1 | 8/2013 | Saettel et al. |
| 2013/0225683 A1 | 8/2013 | Gagnon et al. |
| 2013/0233727 A1 | 9/2013 | Tsai et al. |
| 2013/0245547 A1 | 9/2013 | El-Khatib et al. |
| 2013/0267796 A1 | 10/2013 | Enric Monte Moreno |
| 2013/0281796 A1 | 10/2013 | Pan |
| 2013/0282301 A1 | 10/2013 | Rush |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0037749 A1 | 2/2014 | Shea et al. |
| 2014/0057331 A1 | 2/2014 | Tajima et al. |
| 2014/0066735 A1 | 3/2014 | Engelhardt et al. |
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |
| 2014/0349256 A1 | 11/2014 | Connor |
| 2014/0349257 A1 | 11/2014 | Connor |
| 2014/0356420 A1 | 12/2014 | Huang |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |
| 2015/0025903 A1 | 1/2015 | Mueller-Wolf |
| 2015/0031053 A1 | 1/2015 | Moerman |
| 2015/0037406 A1 | 2/2015 | Martinez et al. |

FOREIGN PATENT DOCUMENTS

| | | |
|---|---|---|
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1115389 A1 | 7/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 2139393 A2 | 1/2010 |
| EP | 2300046 A2 | 3/2011 |
| EP | 2352456 A1 | 8/2011 |
| EP | 2355669 A2 | 8/2011 |
| EP | 2377465 A1 | 10/2011 |
| EP | 2384750 A1 | 11/2011 |
| EP | 2418972 A1 | 2/2012 |
| EP | 2448432 A1 | 5/2012 |
| EP | 2448468 A1 | 5/2012 |
| EP | 2482712 A1 | 8/2012 |

(56) References Cited

FOREIGN PATENT DOCUMENTS

| | | |
|---|---|---|
| EP | 2535831 A1 | 12/2012 |
| EP | 2552313 A2 | 2/2013 |
| EP | 2585133 A1 | 5/2013 |
| EP | 2590559 A2 | 5/2013 |
| EP | 2596448 A1 | 5/2013 |
| EP | 2603133 A1 | 6/2013 |
| EP | 2640373 A1 | 9/2013 |
| EP | 2641084 A1 | 9/2013 |
| EP | 2654777 A2 | 10/2013 |
| EP | 2659407 A1 | 11/2013 |
| EP | 2666369 A1 | 11/2013 |
| EP | 2685895 A1 | 1/2014 |
| EP | 2720713 A2 | 4/2014 |
| EP | 2736404 A1 | 6/2014 |
| EP | 2742447 A2 | 6/2014 |
| EP | 2742449 A2 | 6/2014 |
| EP | 2745225 A2 | 6/2014 |
| EP | 2760335 A1 | 8/2014 |
| EP | 2763722 A2 | 8/2014 |
| EP | 2798548 A1 | 11/2014 |
| EP | 2822647 A1 | 1/2015 |
| WO | 1992019260 A1 | 11/1992 |
| WO | 1996009823 A1 | 4/1996 |
| WO | 1999044496 A1 | 9/1999 |
| WO | 2002036139 | 5/2002 |
| WO | 2003024468 | 3/2003 |
| WO | 2003077895 | 9/2003 |
| WO | 2003094927 | 11/2003 |
| WO | 2005081119 A2 | 9/2005 |
| WO | 2005081170 A2 | 9/2005 |
| WO | 2005081171 A2 | 9/2005 |
| WO | 2005081173 A1 | 9/2005 |
| WO | 2006022619 A2 | 3/2006 |
| WO | 2006022629 A1 | 3/2006 |
| WO | 2006022633 A1 | 3/2006 |
| WO | 2006022634 A1 | 3/2006 |
| WO | 2006022636 A1 | 3/2006 |
| WO | 2006022638 A1 | 3/2006 |
| WO | 2006044556 A2 | 4/2006 |
| WO | 2003101177 | 7/2006 |
| WO | 2006079124 A2 | 7/2006 |
| WO | 2006091918 A2 | 8/2006 |
| WO | 2006130901 A1 | 12/2006 |
| WO | 2007149533 A2 | 12/2007 |
| WO | 2008005761 A2 | 1/2008 |
| WO | 2008013324 A1 | 1/2008 |
| WO | 2008124478 | 10/2008 |
| WO | 2011094352 A1 | 8/2011 |
| WO | 2012047800 A1 | 4/2012 |
| WO | 2012065556 A1 | 5/2012 |
| WO | 2012097064 A1 | 7/2012 |
| WO | 2012148252 A2 | 11/2012 |
| WO | 2012161670 A2 | 11/2012 |
| WO | 2013040712 A1 | 3/2013 |
| WO | 2013050309 A1 | 4/2013 |
| WO | 2013086372 A1 | 6/2013 |
| WO | 2013108262 A1 | 7/2013 |
| WO | 2013134548 A2 | 9/2013 |
| WO | 2013172833 A1 | 11/2013 |
| WO | 2013177565 A1 | 11/2013 |
| WO | 2014011488 A2 | 1/2014 |
| WO | 2014012084 A1 | 1/2014 |
| WO | 2014023834 A2 | 2/2014 |
| WO | 2014024201 A1 | 2/2014 |
| WO | 2014028607 A1 | 2/2014 |
| WO | 2014068007 A1 | 5/2014 |
| WO | 2014075135 A1 | 5/2014 |
| WO | 2014099829 A1 | 6/2014 |
| WO | 2014106263 A2 | 7/2014 |
| WO | 2014145049 A2 | 9/2014 |
| WO | 2014149535 A1 | 9/2014 |
| WO | 2014149781 A1 | 9/2014 |
| WO | 2014152704 A1 | 9/2014 |
| WO | 2014162549 A1 | 10/2014 |
| WO | 2014164226 A2 | 10/2014 |
| WO | 2014179171 A1 | 11/2014 |
| WO | 2014187812 A1 | 11/2014 |
| WO | 2014190231 A1 | 11/2014 |
| WO | 2014202024 A1 | 12/2014 |
| WO | 2014209630 A2 | 12/2014 |
| WO | 2014209634 A1 | 12/2014 |

\* cited by examiner

SYSTEM AND METHOD FOR OPTIMIZING INSULIN DOSAGES FOR DIABETIC SUBJECTS

CROSS REFERENCE TO RELATED APPLICATIONS

This U.S. patent application is a continuation of, and claims priority under 35 U.S.C. § 120 from, U.S. patent application Ser. No. 15/862,819, filed on Jan. 5, 2018, which is a continuation of U.S. patent application Ser. No. 13/610,287, filed on Sep. 11, 2012. The disclosures of these prior applications are considered part of the disclosure of this application and are hereby incorporated by reference in their entireties.

TECHNICAL FIELD

This invention is directed to a system and method for optimizing the control of blood glucose for diabetic subjects. In particular, this invention is directed to a system incorporating a processor whose logic optimizes the control of the blood glucose of the diabetic subject based upon a subject blood glucose level reading at a particular time period and a meal type having been ingested or to be ingested. Still further, this invention pertains to an optimized control of the blood glucose level for developing a recommended insulin dosage dependent upon a time period defined as a pre-meal, post-meal, bedtime, mid-sleep, or miscellaneous blood glucose reading taken with a standard glucometer. Additionally, this invention pertains to a system which takes into account both the meal type such as breakfast, lunch, dinner, or snack. Further, this invention is directed to a system which utilizes the past history of the subject for a particular meal type and time period to optimize the blood glucose level for the diabetic subject. Still further, this invention pertains to optimization of blood glucose levels based upon estimated carbohydrates to be ingested by the subject at a particular meal type in association with whether or not the subject is on a meal plan.

BACKGROUND

Diabetes is a growing problem in the world. Conventional treatment for diabetes requires that the patient measures his/her blood glucose several times a day with a glucometer. The patient then estimates the number of units of insulin that should be injected to prevent either hypoglycemia (too low blood glucose) or hyperglycemia (too high blood glucose) based upon the blood glucose reading and the type of food that the patient has ingested or expects to ingest. This generally is a trial and error solution which may have deleterious effects.

Diabetes or diabetes mellitus is a generally chronic disorder of glucose or sugar metabolism. This is generally caused by the inadequate production of insulin or inadequate use of the insulin generated. Insulin is a hormone produced in specialized cells in the pancreas which permits the body to use and store glucose. Diabetes is a leading cause of death in the World.

Lack of insulin for a subject results in the inability to metabolize glucose and the capacity to store glycogen in the liver and active transport of glucose across cell membranes are impaired Symptoms of diabetes or diabetes mellitus results in elevated sugar levels in the urine and blood, as well as increased urination, thirst, hunger, weakness, and weight loss. Prolonged excess blood glucose levels (hypoglycemia) leads to increased protein and fat catabolism which may cause premature vascular degeneration and atherosclerosis. Where diabetes is not controlled, such leads to diabetic acidosis where ketones are built up in the blood.

Diabetes affects the body handling of fats which may lead to fat accumulation in the arteries and potential damage to the kidneys, eyes, heart, and brain. Thus, there is a great need for accuracy in controlling the blood glucose level of a diabetic subject to optimize the blood glucose level and have the subject maintain a stable blood glucose level within safe limits.

The optimization of blood glucose levels for a diabetic subject is a function of numerous interdependent parameters associated with time periods, meal types, ingested food products, prior history of the diabetic subject at respective time periods and meal types being ingested or to be ingested, as well as the physical condition of the subject. In order to optimize the insulin dosage to be administered to a subject, the interdependent parameters each having an effect on the other, have to be taken into account to produce a recommended insulin dosage level.

Thus, the subject system has been developed in order to optimize the insulin dosage recommended for a subject at a particular time period and further associated with a meal type based upon the above-referenced interrelated parameters.

PRIOR ART

Prior systems for recommending insulin dosage suffer from the fact that the previous history of the subject are not generally taken into account with respect to a particular time period and meal type either ingested or to be ingested.

Conventional treatments for diabetes require that the patient measure his/her blood glucose a predetermined number of times during a day with a standard glucometer. The patient may then estimate the number of units of insulin that he/she should inject for prevention of either hypoglycemia or hyperglycemia.

It is difficult for the diabetic subject to accurately estimate the number of grams of carbohydrates that he/she will ingest and in general the interrelated aforementioned parameters are not taken into account for optimizing glycemic control.

Thus, there is a great need for a system which calculates an optimized blood glucose level and insulin dosage to be recommended to the subject based upon a current blood glucose reading in association with a meal type, time period, physical condition, and previous history of blood glucose levels.

SUMMARY

One aspect of the disclosure provides [an independent claim].

The subject system provides a system and method for optimizing the glycemic control of a diabetic subject based upon his/her past glycemic history and provides an optimized guidance as to the number of units of insulin or insulin dosage to be injected at any time depending on an extended set of factors. Each of these factors can affect the patient's need for insulin.

The diabetic patient or caregiver inserts base data into a computer system for estimating the number of grams of carbohydrates that the patient is about to ingest or has ingested at a particular meal type. The meal type and time period is further input as manual data inserted into the computer system.

Based upon the input data as to the current blood glucose reading and the aforementioned input data, the subject system calculates an insulin dosage which is optimized for the patient's particular condition at the current time.

One of the features of the subject system is that such provides for the patient the optimum number of units of insulin to be injected dependent on the subject's past history of blood glucose results under similar circumstances. As an example, if the subject measures a blood glucose rating of 100 mg/dl, such is input into the system and indicates to the system that there is an estimated ingestion of 30 grams of carbohydrates to be ingested or has previously been ingested, and the system states that 15 units of insulin should be injected, and then the next reading of blood glucose is 70 mg/dl, such would result in an undesirably low reading. At a subsequent time that the subject takes the same or similar blood glucose reading and the number of grams of carbohydrates to be eaten is inserted, then the system knowing that 15 units of insulin is too high a dose, the system may suggest 13 units of insulin to prevent a low reading of blood glucose. Thus, an important feature of the subject system is that the patient's prior glycemic history is stored by the system and subsequently used in calculations for recommending insulin to be injected dependent upon prior results experienced by the specific subject.

DETAILED DESCRIPTION

Figure 1:
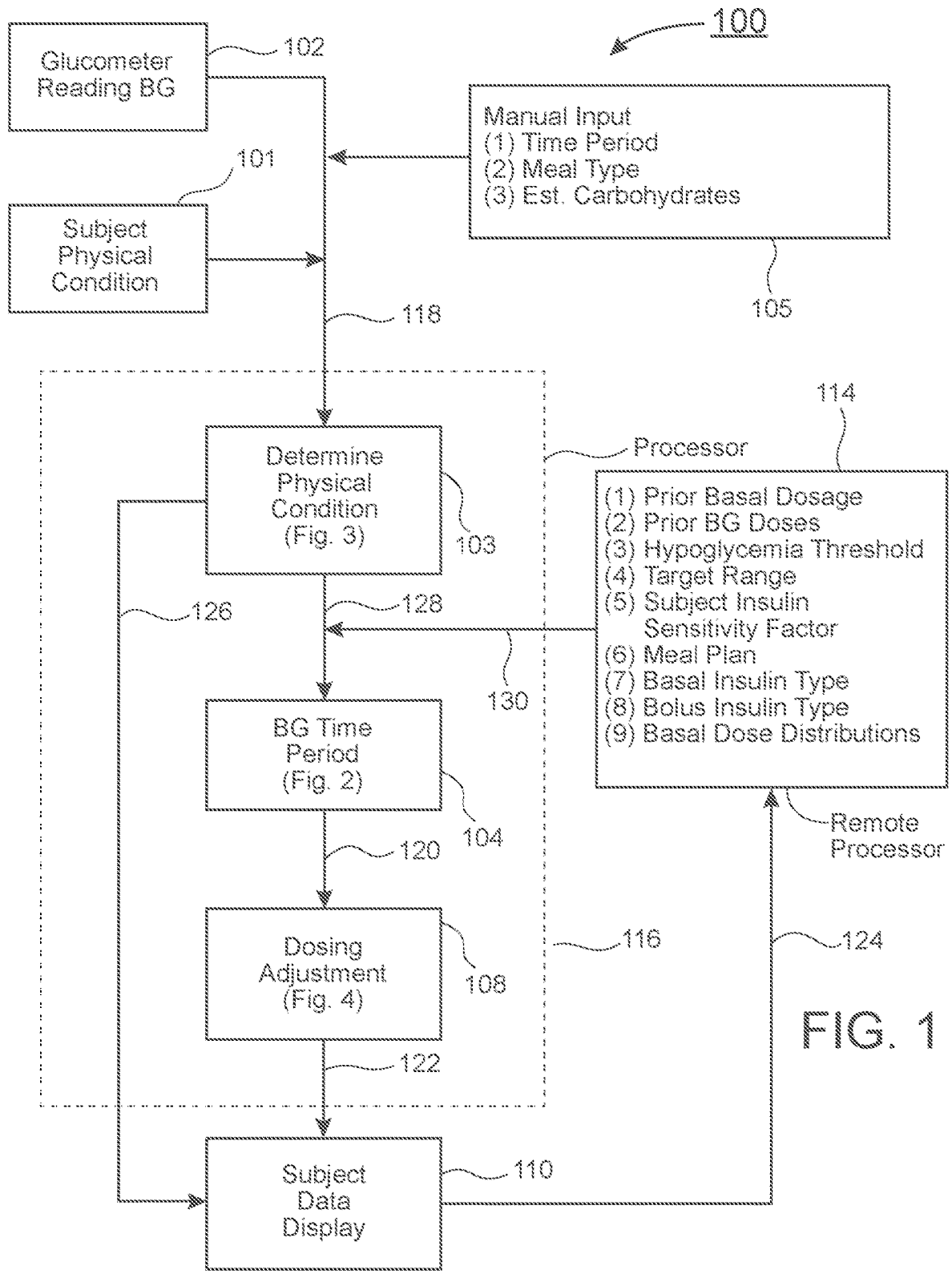
FIG. 1 is a broad flow block diagram of the computer system for processing and calculating insulin dosages to be administered to a subject responsive to a particular meal type and a predetermined time period.

Referring now to FIG. 1, there is shown blood glucose in insulin dosage administering system 100 for determining an insulin dosage value to be administered to a subject. In particular, system 100 is directed to calculating, processing and recommending blood glucose levels for diabetic subjects at specific times prior to or subsequent to ingestion of food or other nutrients and calculating a recommended insulin dose to be administered. System 100 is designed to provide the subject with calculated insulin dosage instructions based upon nutritional and physical information in combination with the personal history of previous insulin administration and resulting blood glucose levels.

The following definitions of the terminology used in the following paragraphs are as follows:

Mid-point target blood glucose range ($T_m$) shall refer to the mid-point of a target blood glucose range (or other blood glucose value within the range) inserted into remote processor 114 by a physician or caregiver for a subject. Although referring to "mid-point" of the blood glucose range, the mid-point target data may be inserted as a function of the mid-point of the mid-point target blood glucose range or some other input deemed appropriate by the subject's physician or caregiver.

Time periods shall refer to the time that a subject is taking a blood glucose reading with a standard glucometer and further refers to a pre-meal time period, a post-meal time period, a bedtime period, a mid-sleep time period, or some miscellaneous time period when the subject is taking the blood glucose reading.

Meal type shall refer to either breakfast, lunch, dinner, snack, or miscellaneous associated with when the subject is taking the subject's blood glucose reading.

Blood glucose reading shall be the blood glucose reading taken at a predetermined time period and associated with a meal type.

Bolus shall refer to recommended insulin dose administered for a meal type and a time period.

Basal Dose shall refer to a total basal dosage of insulin to be taken for one day.

Hypoglycemia threshold shall refer to a lower blood glucose value for a particular subject provided by a physician or other caregiver.

Prior blood glucose doses and/or levels shall refer to previous blood glucose doses and/or levels taken or calculated at previous time periods associated with a respective meal type.

Basal insulin type shall refer to the type or brand of long acting insulin used with basal dose calculations.

Bolus insulin type shall refer to the type or brand of short acting insulin used with meal bolus and correction doses of insulin.

Basal dose distribution shall refer to the frequency and distribution of basal doses for a particular day such as (1) once a day (SID); (2) twice a day (BID); or, (3) three times a day (TID).

Physical condition parameter shall refer to a physical condition of the subject at the time that the blood glucose reading is being taken such as whether or not the subject is exercising or plans to exercise.

Intermediate blood glucose correction dosage shall refer to a first calculation by processor 116 shown in FIG. 1.

Carbohydrate to insulin ratio is a subject specific factor based upon a function of the total daily dose of insulin based upon the subject's weight at the time of initialization of the system 100 processes.

Meal plan shall refer to whether or not the subject is limited to ingesting a known number of carbohydrates for each meal type. When a subject is "on" a meal plan, the subject is generally prescribed a predetermined number of carbohydrates to be ingested at a selected meal type.

Miscellaneous time period shall refer to blood glucose calculations at a time period which is not associated with the time periods of breakfast, lunch, dinner, or snack. Such a miscellaneous time period may be associated with a subject fasting period when blood glucose calculations are being processed.

Mid-sleep time period shall refer to blood glucose readings taken at a time during a time period when the subject is normally asleep, generally at some point during a sleeping cycle of the subject.

Insulin sensitivity factor shall refer to a subject specific sensitivity to insulin, generally determined by a physician or care giver and inserted as a portion of the data stored in the remote processor.

System processor shall refer to an on-site processor which calculates a user's recommended insulin dosage value to be taken at a selected time period and a selected meal type.

Remote processor shall refer to a processor which is coupled to the system processor and stores a first set of a subject's blood glucose parameters and includes but is not limited to prior basal and bolus dosages, prior or previous blood glucose readings for selected meal types and time periods, subject specific hypoglycemia thresholds, prescribed mid-point of a subject's target range, a subject specific insulin sensitivity factor, basal insulin type, bolus insulin type, basal dose distributions, and the number of carbohydrates a subject is recommended to ingest for a selected meal type. The remote processor is generally locationally removed (but in communication) with the system processor, however in some cases the remote processor may be incorporated with the system processor.

Referring now to FIG. 1, there is shown blood glucose system 100 for calculating, processing, determining, and displaying a recommended insulin dosage value (bolus) to be administered to a subject. The broad block diagram shown in FIG. 1 includes a glucometer reading (BG) which is inserted by the subject in block 102. The subject takes his/her blood glucose value with a standard glucometer well-known in the art and commercially available. The glucometer generally provides the subject's current blood glucose reading in mg/dl.

Further, data is inserted by the subject in block 101 as to the physical condition of the subject at the time of the taking of the blood glucose value. The data inserted in block 101 will further be described throughout the flow process and in particular with regard to FIG. 3. In general, data inserted into block 101 includes whether the subject is currently exercising or plans to exercise. Further, data is stored in remote processor 114 associated with prior basal dosages, prior blood glucose doses administered for particular meal types and time periods (bolus), a subject specific hypoglycemia threshold determined by the physician. Data to be included in block 105 is the estimated number of carbohydrates the subject will be ingesting at a particular meal type if the subject is not on a meal plan, as well as the number of carbohydrates recommended to be ingested for a particular meal type if the subject is on a prescribed meal plan. Further included in the data stored in remote processor 114 is the mid-point, target blood glucose range and the mid-point ($T_m$) inserted by a physician or other caregiver for a particular subject.

The blood glucose reading taken in block 102 and the subject physical condition in block 101 is inserted into processor 116 on line 118. Within block 103, a determination of the physical condition of the subject is made independent of further calculations within processor 116 to be further detailed in relation to FIG. 3. Block 103 directs processor 116 to decision block 302 in FIG. 3 where the subject indicates whether his condition is exercise. If the condition in decision block 302 is that the subject is not exercising and does not plan to exercise, the information flows on information line 320 back to block 104 in FIG. 1 for further calculations to be further described in following paragraphs.

Figure 4:
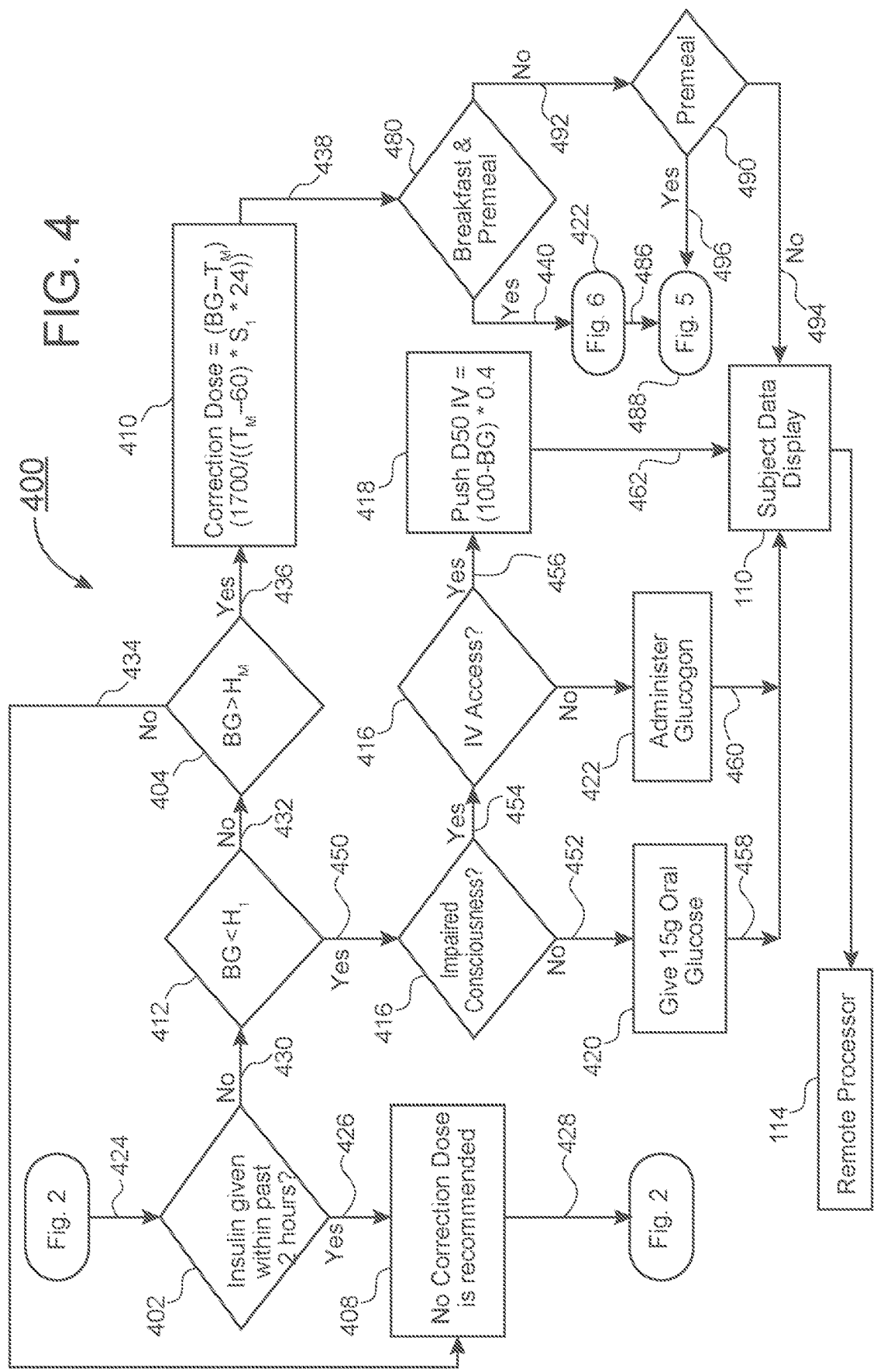
FIG. 4 is a flow block diagram associated with determining a correction dosage to be administered to the subject dependent upon input data provided by the subject associated with the meal type and the time period.

From block 104, the information then flows to dosing adjustment 108 detailed in FIG. 4 and then to subject display 110 and to remote processor 114 for storing the data.

Figure 3:
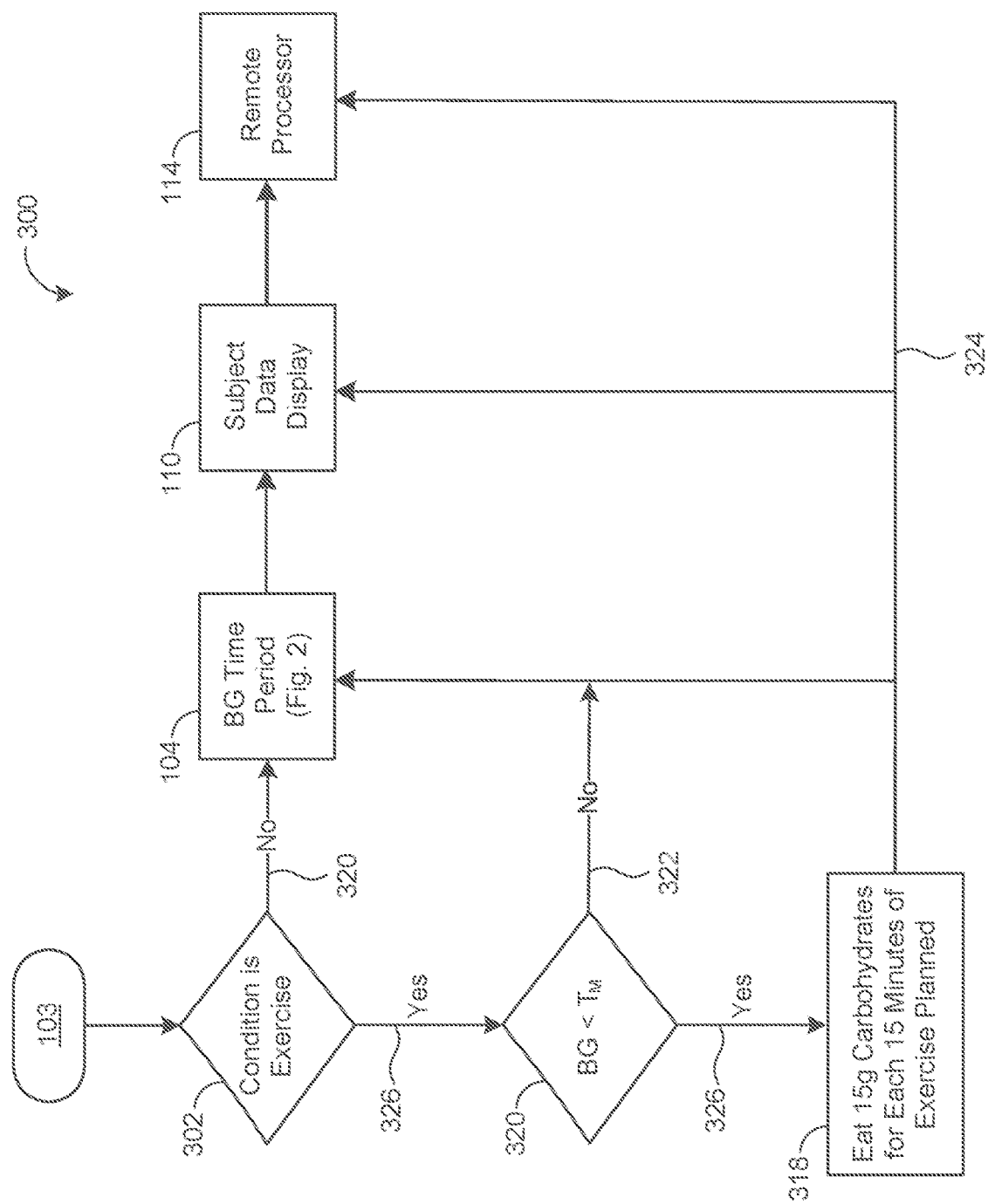
FIG. 3 is an information flow block diagram associated with processing a physical condition of the subject.

If the condition is an exercise condition, found in decision block 302 of FIG. 3, the logic moves on line 326 to decision block 320 where it is determined whether the blood glucose level read in block 102 from the glucometer reading is less than or equal to the mid-point target blood glucose range stored in remote processor 114. If the blood glucose level is equal to or greater than the mid-point target blood glucose range, information is directed on line 322 to block 104 in FIG. 1 for further calculations and passes subsequently to display 110 and remote processor 114.

If the blood glucose level value in decision block 320 is found to be less than the mid-point target blood glucose range, information is directed on line 326 to block 318 where the subject is instructed to eat a predetermined amount of carbohydrates for each predetermined minutes of exercise being planned or having been accomplished. This instruction is then provided to the patient on subject display 110 on line 324 and the information is additionally sent to remote processor 114 for storage of the instructions.

Figure 2:
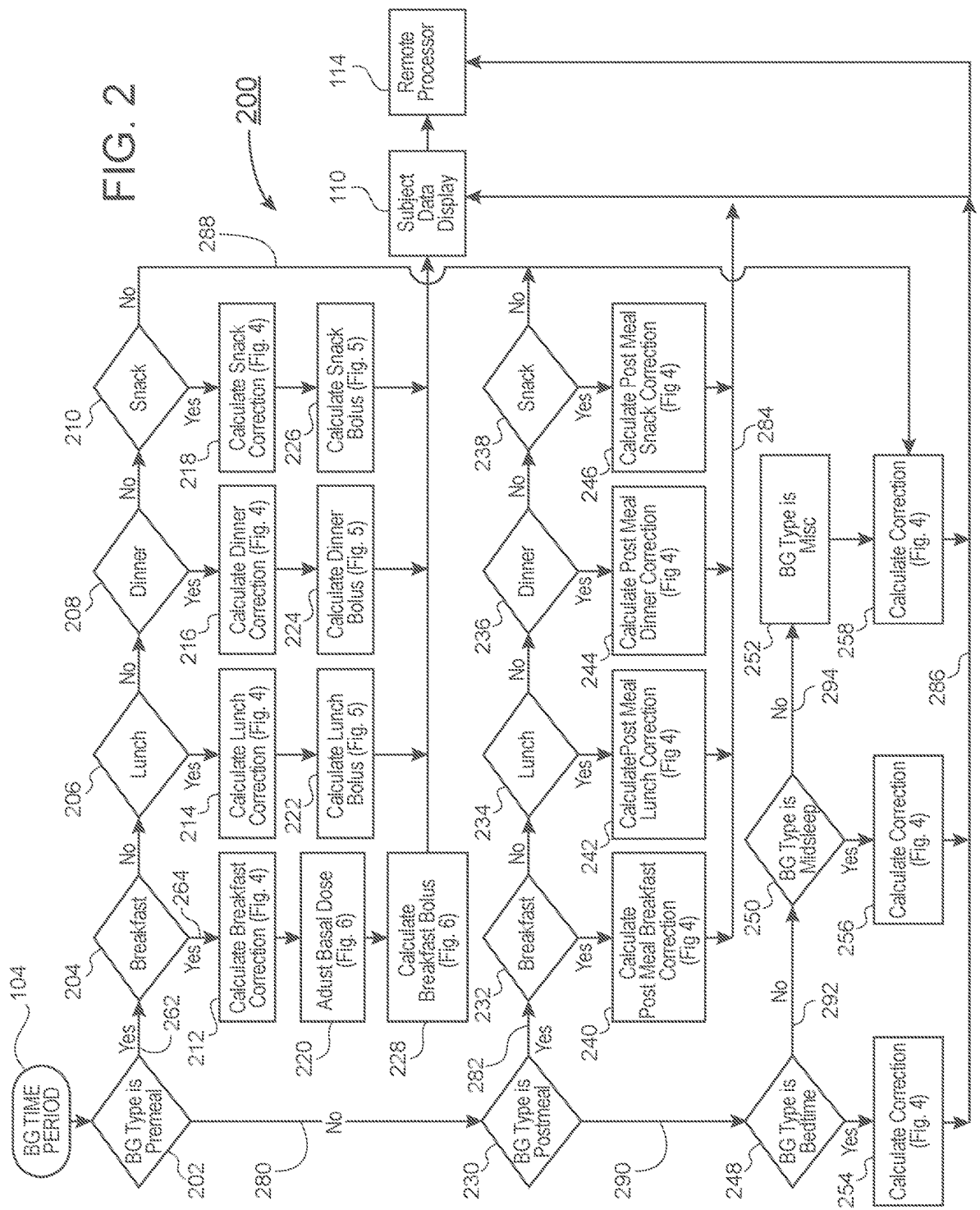
FIG. 2 is a logic block diagram providing a broad logic flow of the logic associated with the computer system and modules dependent upon whether the meal type is pre-meal, post-meal, bedtime, mid-sleep, or miscellaneous.

Thus, whether the condition is exercise determined in decision block 302, or whether or not the blood glucose level is less than the mid-point of the target blood glucose range determined in decision block 320, all logic then passes to blood glucose time period block 104 shown in FIG. 1 where the processing of block 104 is initiated in FIG. 2.

Once an intermediate processing or correction dosage calculation is completed in FIG. 2 for a particular meal type and time period, the logic flows on line 120 (FIG. 1) to dosing adjustment block 108 which is calculated in FIG. 4 to be further detailed and described. Once the dosing adjustment in block 108 has been made by processor 116, information flows on line 122 to subject data display 110 for providing a visual, audio or other type of sensory indication to the subject as to the recommended insulin dosage to be administered. In overall concept, the information provided on line 122 to data display 110 is then transported to remote processor 114 on line 124 for storage of all data calculated. Remote processor 114 stores prior basal dosages, prior administered blood glucose doses (bolus), hypoglycemia threshold, and mid-point target blood glucose range ($T_M$) which are transmitted to processor 116 on line 130 for processing.

Returning back to block 103, which has been detailed in the description of FIG. 3, all information with regard to the physical condition of the subject is additionally transported on line 126 to subject data display 110 simultaneous with the information flowing on line 128 into block 104 for determination of the blood glucose time period.

System processor 116 and subject data display 110 may be incorporated within a standard Personal Computer System which has a standard monitor screen for permitting the subject to visually obtain the recommended insulin dosage value being calculated within the system processor 116 and/or the remote processor 114. The subject display monitor 110 generally provides visual data to the user, however, as is known, audio information may also be transmitted to the subject.

Referring now to FIGS. 2 and 4-7, when the information flows into block 104, the logic initially is directed to FIG. 2 where a decision is made as to whether the time period at which the blood glucose level has been taken is determined to be pre-meal, post-meal, bedtime, mid-sleep, or miscellaneous.

Information flow from within block 104 of FIG. 1 is inserted on line 260 to decision block 202 for determining whether the blood glucose reading taken is pre-meal. If the blood glucose reading is taken prior to breakfast, lunch, dinner, or snack, then information flows on line 262 to decision block 204 to determine whether the meal type of the pre-meal time period is breakfast.

If it is determined in decision block 204 that the pre-meal type is breakfast, then the logic is transported on line 264 to block 212 for calculation of a blood glucose correction dosage or intermediate blood glucose correction dosage. Block 212 includes the processing of the logic blocks in FIG. 4. The information in block 212 is inserted into decision block 402 on line 424 for determination of whether insulin has been administered within a predetermined time period which is generally 2.0 hours, however, this is adjustable by a physician for a specific subject. If insulin has been administered within a predetermined time period, the logic then moves on line 426 to block 408 where "no correction dose" is recommended and the information returns to FIG. 2 for further processing in block 220.

Where insulin has not been administered within a predetermined time period found in decision block 402, information is directed to decision block 412 on line 430 for determination of whether the instant or current blood glucose level reading from the glucometer in block 102 is less than the hypoglycemia threshold value stored in block 114. If the blood glucose reading is equal to or greater than the hypoglycemia threshold value, information is transported on line 432 to decision block 404 where a determination is made whether the blood glucose reading is greater than the mid-point of the target blood glucose range ($T_M$).

If it is determined that the blood glucose reading is less than the mid-point of the target blood glucose range, information is directed on line 434 back to block 408 where there is "no correction dose recommended" and the information flows back to FIG. 2 for further processing on line 428 in block 220.

Where it is determined that the blood glucose reading is greater than the mid-point of the target blood glucose range in block 404, the logic then passes on line 436 to calculation block 410 where the intermediate correction or correction insulin dosage is calculated. The intermediate blood glucose correction dosage calculated in block 410 is a function of the blood glucose reading, the mid-point of the blood glucose target range, and the subject sensitivity factor in accordance with the formula:

$$CD = \frac{(BG - T_m)}{(1700((T_m - 60) \times S_1 \times 24))} \quad (1)$$

Where: CD=correction dose calculated (units of insulin)
BG=blood glucose reading (mg/dl)
$T_m$=mid-point of blood glucose target range (mg/dl)
$S_1$=patient insulin sensitivity factor (units/mg/dl)

Once the blood glucose correction dosage is determined in calculation block 410, information is directed to decision block 480 on line 438. Since the correction dosage and associated logic of FIG. 4 is used in conjunction with all time periods where the blood glucose value is taken including pre-meal, post-meal, bedtime, mid-sleep, and miscellaneous, as well as meal types, breakfast, lunch, dinner, snack, bedtime and mid-sleep, the information on line 438 is inserted into the decision block 480 where it is once again determined whether the meal type and the time period is breakfast and pre-meal.

Figure 5:
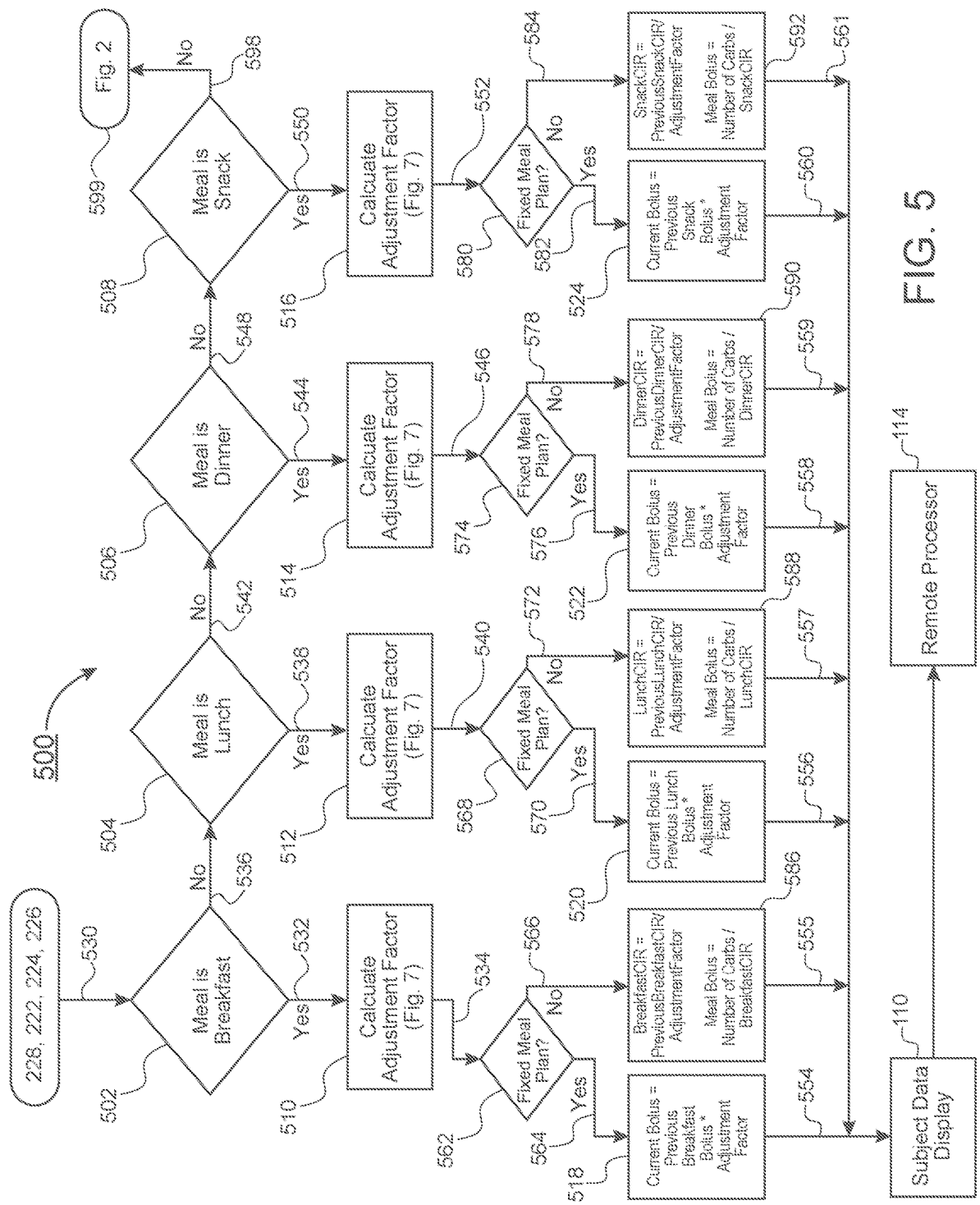
FIG. 5 is a logic flow diagram for calculation of the current bolus associated with an adjustment factor.
Figure 6:
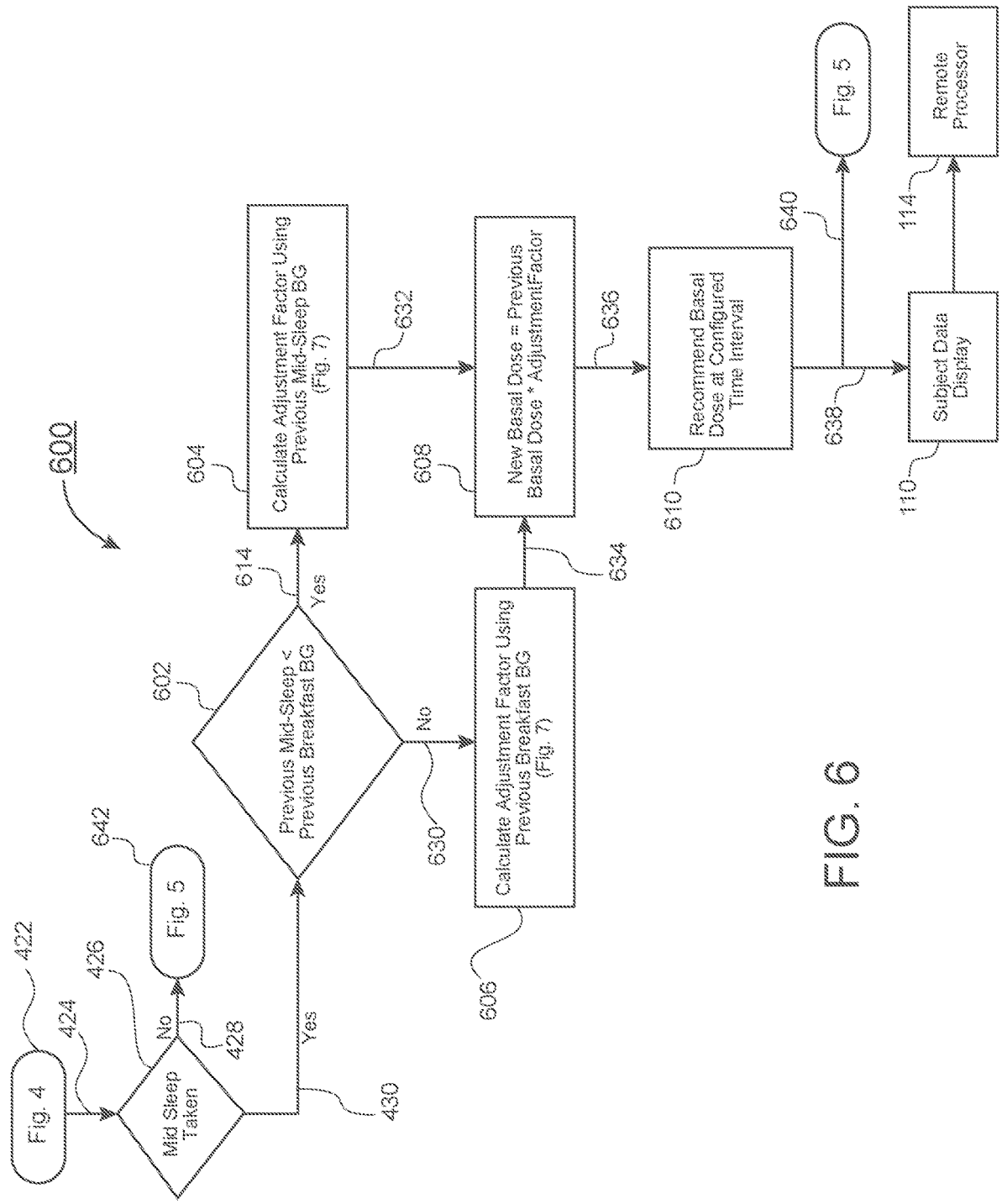
FIG. 6 is a flow block diagram showing the processing for calculating updated basal dosages; and, FIG. 7 is a flow block diagram showing the adjustment factor calculations based upon current blood glucose levels.

If both of the conditions are met (e.g., meal type is pre-meal and time period is breakfast), information then is directed on line 440 to transfer block 422 which is representative of FIG. 6. Referring now to FIG. 6, information from transitional block 422 passes on line 424 into decision block 426 to determine whether a previous mid-sleep blood glucose level has been determined and stored in either system processor 116 and/or remote processor 114. If there is no previous mid-sleep blood glucose level available or the subject does not take mid-sleep blood glucose readings, information passes on line 428 to transfer block 642 for further processing in FIG. 5.

If there is a previous mid-sleep blood glucose level availability, information is directed on line 430 to decision block 602 to determine whether the previous mid-sleep blood glucose level was less than the previous breakfast blood glucose level reading stored in remote processor 114. If the previous mid-sleep blood glucose level is less than or equal to the previous breakfast blood glucose level, the logic passes on line 614 to calculation block 604 for calculating an adjustment factor using the previous mid-sleep blood glucose level.

Figure 7:
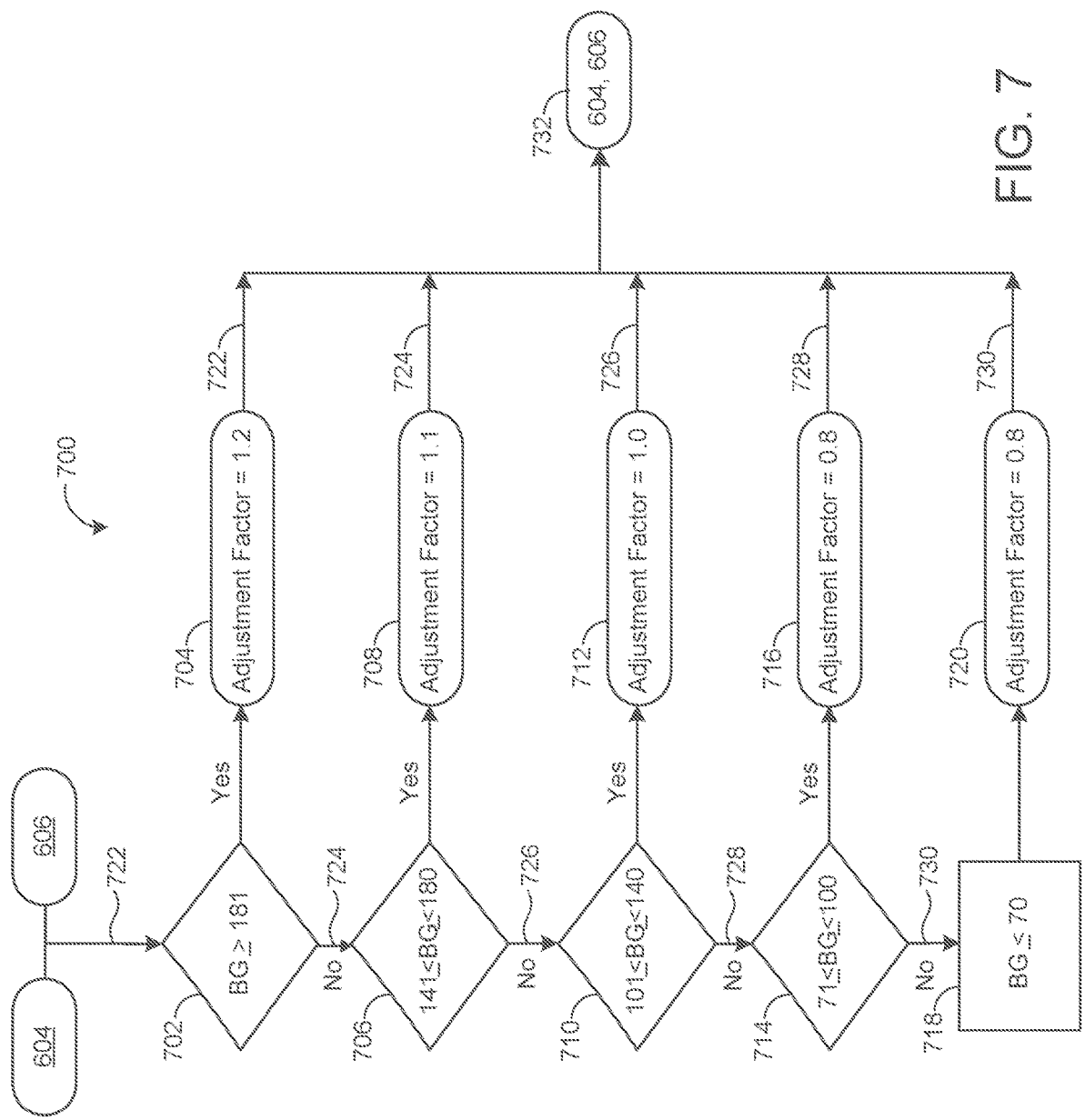

Calculation of the adjustment factor using the previous mid-sleep blood glucose level is shown in FIG. 7 to be further detailed. Block 604 calculations decision blocks are made in 702, 706, 710, and 714, as well as calculation block 718 which provides for a particular adjustment factor associated with the blood glucose reading. The information is then passed to block 608 in FIG. 6 for a Basal dose to be calculated based upon the adjustment factor.

If the previous mid-sleep blood glucose level is greater than the previous breakfast blood glucose level in decision block 602, information is transported on line 630 to processing block 606 where the adjustment factor is calculated using the previous breakfast blood glucose level in accordance with the adjustment factor found in FIG. 7. Thus, in both processing block 604 and 606, an adjustment factor is calculated in the logic flow associated with FIG. 7.

Calculation blocks 604 and 606 are calculated in FIG. 7 where the information flows on line 722 to initial decision block 702 to determine whether the blood glucose level is greater than or equal to 181 mg/dl. If the blood glucose level is greater than 181 mg/dl, then an adjustment factor is set in block 704 as being 1.2. If the blood glucose level is not greater than or equal to 181 mg/dl, then information flows on line 724 to decision block 706 where it is determined whether the blood glucose level is within the range of 141 mg/dl to 180 mg/dl. If the blood glucose level is within the range defined in decision block 706, the adjustment factor is set to be 1.1 in block 708. If the blood glucose level is not within the range determined in decision block 706, information is transported on line 726 to decision block 710 where it is determined whether the blood glucose level is greater than or equal to 101 mg/dl and less than or equal to 140 mg/dl. If the blood glucose level is within the range defined in block 710, the adjustment factor is set in block 712 as 1.0. If the blood glucose level does not fall within the range associated with decision block 710, information is directed on line 728 to decision block 714 where it is determined whether the blood glucose level is within the range of 71 mg/dl to 100 mg/dl. If the blood glucose level is within the range defined in block 714, the adjustment factor is set in block 716 to be 0.8. If the blood glucose level is not within the range associated with the decision made in decision block 714, the blood glucose level must be less than or equal to 70 mg/dl as shown in block 718 and in this case, the adjustment factor is set in block 720 as 0.8. The adjustment factors set in blocks 704, 708, 712, 716, and 720 are dimensionless.

Once the proper adjustment factor is defined in blocks 704, 708, 712, 716, or 720 information flows on respective lines 722, 724, 726, 728, or 730 to transfer block 732 where information returns to either blocks 604 or 606 in FIG. 6.

As stated, the adjustment factor after being calculated in FIG. 7, the information returns to FIG. 6 and in particular to blocks 604 and 606. The information in block 604 and 606 respectively pass on lines 632 or 634 to calculation block 608 where the new basal dose is calculated. The new basal dose calculated in block 608 is the previous basal dose multiplied by the adjustment factor and this value is inserted into block 610 to recommend the basal dose at the configured time interval. Information then flows on line 636 to block 638 to insert the recommended basal dose to the subject data display 110 and storage in the system processor 116 and/or remote processor 114, as well as being returned on line 640 for further calculations of either the breakfast, lunch, dinner, or snack bolus associated with the logic flow in FIG. 5.

Thus, as shown in FIG. 4, if it is determined that both conditions of the time period being pre-meal and the meal type is breakfast, information is passed on line 440 to transfer block 422 for calculations in FIG. 6 and then the information is inserted into transfer block 488 for processing in accordance with the logic described in FIG. 5.

Returning now to FIG. 4, where once the correction dosage has been calculated in block 410, and the information passed to decision block 480, if it is determined in block 480 that both conditions of the time period being pre-meal and the meal type being breakfast are not met, logic flows on line 492 to decision block 490. Decision block 490 determines whether the time period is pre-meal. If the time period is pre-meal the logic moves on line 496 to transfer block 488 for processing in FIG. 5. If the time period is not pre-meal then the logic flow is directed to block 110 in FIG. 1 and the correction dose is inserted in accordance with the calculations made in calculation block 410.

Returning back to FIG. 4 and decision block 412, if it is determined in decision block 412 that the blood glucose level is less than the hypoglycemia threshold level, information flows on line 450 to decision block 414. In decision block 414, it is determined whether the subject has impaired consciousness, and if the subject does not have impaired consciousness information flows on line 452 to block 420 where the subject is instructed to be given a predetermined dosage of oral glucose and data is then sent directly to data display block 110. If the subject has impaired consciousness found in decision block 414, information flows on line 454 to decision block 416 where it is determined whether there is IV access. If there is IV access, information on line 456 is inserted into block 418 where instructions are provided to give a D50IV=(100-BG)×0.04 amount to the subject. If there is no IV access, glucogen is then recommended to be administered in block 422. Information from blocks 420, 422, and 418 are passed on lines 458, 460, and 462 for information input to data display 110 and subsequently inserted into remote processor 114 of FIG. 1.

Returning now to FIG. 2, once the basal dose has been adjusted in block 220 as associated with the processing in FIGS. 6 and 7, for a time period which is pre-meal and a meal type which is breakfast, information is directed to block 228 for calculation of the recommended insulin dosage at breakfast or breakfast bolus.

Similarly, if the time period is pre-meal and meal type is lunch, calculations of the intermediate blood glucose correction dosage for lunch is calculated in FIG 4. If the time period is pre-meal and the meal type is dinner, calculation of the intermediate blood glucose correction dosage is made in block 216. Similarly, if it is determined that the time period is pre-meal and that the meal type is a snack in decision block 210, a calculation of the blood glucose correction dosage for the snack is calculated in block 218.

In all processing and calculation blocks 212, 214, 216, and 218, the calculations are provided in association with the previous logic flow description given for the logic blocks in FIG. 4.

Information from FIG. 2 processing blocks 228, 222, 224, and 226 are calculated in accordance with the logic flow in FIG 5. Calculation of the breakfast, lunch, dinner, or snack bolus is shown in FIG. 5 with information passing from blocks 228, 222, 224, and 226 on line 530 to decision block 502 where it is once again determined whether the pre-meal time period is breakfast. If the pre-meal time period is breakfast, information passes to calculation block 510 on line 532 for calculation of the adjustment factor as previously detailed in the logic flow provided for FIG. 7.

If the time period is pre-meal and the meal type is breakfast, calculation of the adjustment factor is made in block 510 in accordance with FIG. 7 as previously discussed. Information then passes to decision block 562 where there is a determination of whether the subject is on a fixed meal plan. If it is determined that the subject is on a fixed meal plan, such as substantially the same number of carbohydrates to be ingested at each time period and meal type, information then passes on line 564 to calculation block 518 which calculates the current bolus in accordance with the equation:

$$CB = CB_i \times AF \quad (2)$$

Where:

CB=current bolus (units of insulin)

$CB_i$=previous bolus administered at the previous Meal type and time period (units of insulin)

AF=adjustment factor (dimensionless)

The current bolus is then passed on line 554 to subject data display 110 and eventually to remote processor 114 as provided in FIG. 1. If it is determined that the subject is not on a fixed meal plan in decision block 562, information is directed through line 566 to calculation block 586 where a number of calculations are performed. Initially, the total prescribed daily basal dose of insulin in units of insulin per day is calculated (TDD) in accordance with the formula:

$$TDD = TDD_M \times W_S \quad (3)$$

Where:

TDD=total prescribed daily basal dose of insulin (units of insulin)

$W_S$=weight of subject (Kg.)

$TDD_M$=subject's Total Daily Dose Multiplier (a weighting factor having dimensions of (units per Kg/day). Typically 0.25 for pediatric subjects, 0.3 for subjects with renal insufficiency, 0.5 for adult subjects, or another subject specific number)

Once the total prescribed daily basal dose is calculated in equation (3), within block 586, the meal of bolus (CB) is calculated by first calculating the carbohydrate to insulin ratio (dimensionless) in accordance with the formula:

$$CIR = 450 \times TDD \quad (4)$$

Where:
CIR=current carbohydrate to insulin ratio (dimensionless)
TDD=total prescribed basal dose of insulin (units of insulin)

Using the previous selected pre-meal CIR to calculate the instant CIR for a particular meal type is made in accordance with the formula:

$$CIR_{B,L,D,S} = \frac{CIR_{B,L,D,S}}{AF} \quad (5)$$

Where: $CIR_{B,L,D,S}$=instant carbohydrate to insulin ratio for a selected meal type of breakfast, lunch, dinner, or snack
$CIR_{B,L,D,S}$=previous carbohydrate to insulin ratio for previous selected meal type of breakfast, lunch, dinner or snack
AF=adjustment factor Finally, the current bolus to be recommended is derived from the Equation:

$$CB = \frac{C_{EST}}{CIR_{B,L,D,S}} \quad (6)$$

Where: $C_{EST}$=estimated number of carbohydrates to be ingested at the pre-meal time period for the current meal type (mg.)
$CIR_{B,L,D,S}$=calculated carbohydrate to insulin ratio calculated in Equation 5.

Subsequent to the calculation of the current bolus in block 518 or block 586, information passes on respective lines 554 and 555 to subject data display 110 and then to remote processor 114.

If it is determined in decision block 502 that the meal is not breakfast, information is directed on line 536 to decision block 504 where a decision is made as to whether the meal is lunch. If the pre-meal is lunch, then information is passed on line 538 to calculation block 512 for calculation of the adjustment factor in FIG. 7 as previously discussed. Once the adjustment factor has been determined from the logic flow in FIG. 7, information then is transported on line 540 to fixed meal plan decision block 568. Decision block 568, similar to decision block 562, determines whether the subject is on a fixed meal plan and if the subject is on a fixed meal plan, information passes on line 570 to calculation block 520 where the current bolus is calculated in accordance with Equation 2. Where the subject is not on a fixed meal plan as determined in decision block 568, information passes on line 572 to calculation block 588 which calculates the lunch bolus in accordance with Equations 3, 4, 5 and 6 as previously discussed. Subsequently, information passes either on line 556 or 557 to subject display data 110 and remote processor 114.

If it is determined that the meal type is not lunch in decision block 504, information is transported on line 542 to decision block 506 where it is determined whether the meal type is dinner. If the meal type is dinner, information is inserted to calculation block 514 on line 544 for calculation of the adjustment factor provided by the logic in FIG. 7. Once the adjustment factor in FIG. 7 has been calculated, information passes on line 546 to decision block 574 determining whether the subject is on a fixed meal plan. The decision block 574 is similar to decision blocks 562 and 568. If it is determined that the subject is on a fixed meal plan, information is then sent to calculation block 522 on line 576 for calculation of the current bolus (CB) in accordance with Equation 2. If the subject is not on a fixed meal plan as determined in decision block 574, the information enters calculation block 590 for calculation of the dinner meal bolus in accordance with Equations 3, 4, 5 and 6. Information is then sent from either calculation block 522 or block 590 on respective lines 558 and 559 to subject data display 110 and then to remote processor 114.

If it is determined in decision block 506 that the meal is not dinner, information then flows on line 548 to decision block 508 where it is determined whether the meal type is a snack. If it determined in decision block 508 that the meal is a snack, information passes on line 550 to calculation block 516 where the adjustment factor is calculated in accordance with FIG. 7. Information then passes on line 552 to decision block 580 which determines whether the subject is on a fixed meal plan. If the subject is on a fixed meal plan as determined in decision block 580, information passes on line 582 to calculation block 524 where the current bolus is calculated based upon equation 2. If the subject is not on a fixed meal plan, the logic flows through line 584 to calculation block 592 where the current meal bolus is calculated in accordance with Equations 3, 4, 5, and 6. Information from block 524 or block 592 is then transported on either Line 560 or 562 to subject data display system 110 and then to remote processor 114.

In this manner, when the blood glucometer reading is taken as represented by block 102, and the physical condition is input by the subject as represented by block 101, when the time period of the blood glucose reading is taken is pre-meal as is determined in decision block 202, a breakfast, lunch, dinner, and snack bolus is calculated by system 100.

If the meal type is not a snack, then the time period is miscellaneous and passes on line 598 to transfer block 599 where logic is transferred to line 288 in FIG. 2. Processing is then provided in calculation block 258 in accordance with the logic flow in FIG. 4

Returning to FIG. 2, assuming that the blood glucose time period has been determined not to be a pre-meal time period in decision block 202, the information passes on line 280 to decision block 230 where decision block 230 determines whether the time period is a post-meal time. If the time period is determined to be post-meal, information is transported on line 282 to decision block 232 where a decision is determined whether this is a breakfast post-meal glucometer reading. If the inputs provided by the subject is to a time period which is post-meal and the meal type is breakfast, information is then transmitted to calculation block 240 in FIG. 2. In this instance, there is no adjustment of the basal dose as was the case when the time period was pre-meal (previously described) and the meal type was breakfast.

Calculation block 240 directs the information to FIG. 4 where a correction dose is calculated in calculation block 410. All logic blocks have been previously detailed, however, in overview, if insulin has not been given within a predetermined period of time, for example two hours as indicated in decision block 402, and the blood glucose reading is equal to or greater than the hypoglycemia threshold value ($H_1$) as determined in decision block 412, the information is directed to decision block 404 and if the blood glucose reading is determined to be greater than the midpoint target blood glucose range reading, the correction dose is calculated in calculation block 410. Responsively, subsequent to the calculations provided in calculation block 240, the results and calculation of the post-meal breakfast correction is transmitted on line 284 to subject display 110 and remote processor 114 for storage of the data calculated.

Similarly, as has previously been described for the pre-meal type calculations in decision blocks 206, 208, and 210, a decision is made as to the fact whether the post-meal blood glucose reading is taken subsequent to lunch in decision block 234, dinner in decision block 236, or a snack in decision block 238. If it is determined that the post-meal blood glucose reading is subsequent to lunch in decision block 234, the information then is inserted into calculation block 242 for calculation of the post-meal lunch correction as associated with the logic flow previously described for FIG. 4.

If the decision in decision block 234 is that the post-meal was not lunch, the information then is directed to decision block 236 for determination of whether the post-meal blood glucose reading was dinner and if it is dinner, the logic flows to block 244 and correction dosage as well as the subject meal bolus is made in association with FIG. 4.

If the blood glucose post-meal reading is a snack determined in decision block 238, similarly as previously described, the information is directed to calculation block 246 for calculation in the same manner as previously described for the post-meal breakfast, lunch and dinner decisions. Information from blocks 240, 242, 244, and 246 are then provided on line 284 to both subject display 110 and remote processor 114 for storage of the data and display of the recommended correction reading.

If it is determined in decision block 230 that the blood glucose time period is neither a pre-meal nor a post-meal, the information is directed on line 290 to decision block 248 where it is determined whether the blood glucose taken is at the time period of bedtime (prior to sleep).

With the blood glucose reading provided in block 101, the information is directed to calculation block 254 for insert into the logic flow of FIG. 4. The logic in FIG. 4 in overall view, passes into correction dose calculation block 410. The bolus for bedtime is then provided on line 286 (FIG. 2) to both subject display system 110 and remote processor 114 as shown in FIG. 1.

Assuming that the blood glucose type is not found to be bedtime in decision block 248, information is then inserted on line 292 to decision block 250 where the blood glucose reading time period is taken as "mid-sleep". If the blood glucose reading is taken as a mid-sleep type reading, information then is inserted into calculation block 256 where the calculation correction is transmitted to the logic previously detailed for FIG. 4 and then inserted on line 286 to subject display system 110 and remote processor 114 as shown in FIG. 2.

In the event that the blood glucose reading provided in block 101 is not a mid-sleep reading as determined in decision block 250, the information then passes on line 204 to calculation block 252 where the meal type is defined as miscellaneous since it is neither for a breakfast, lunch, dinner, or snack reading. The information in 252 is then directed to calculation block 258 where the bolus is calculated in accordance with FIGS. 4, 5, and 7.

In the event that the blood glucose reading meets the time criteria period of a pre-meal, but is not at breakfast, lunch, dinner, or snack as determined in decision blocks 204, 206, 208, and 210, then the meal type must be "miscellaneous" and the information passes on line 288 into block 252 and 258 for calculation of the correction dosage. As seen in FIG. 2, if the blood glucose reading is post-meal, but is not for breakfast as determined in decision block 232, lunch as determined in decision block 234, dinner as determined in decision block 236, or the snack as determined in decision block 238, again, the information is directed on line 288 to 252 since the reading must be a "miscellaneous" reading. In all cases subsequent to the bolus being determined in 254, 256, and 258, information calculated is then inserted for display in system display 110 and stored in remote processor 114 for further use.

In overall concept, there is provided in FIGS. 1-7 a system for determining the insulin dosage value to be administered to a subject dependent on many interrelated parameters. Input to system 100 includes a glucometer reading taken by the subject at a time period defined by whether the blood glucose reading is taken pre-meal, post-meal, bedtime, or at some miscellaneous time. Remote processor 114 maintains in storage, prior basal dosages, hypoglycemia thresholds, target ranges and mid-points of target ranges, and subject insulin sensitivity factor. The subject provides a manual input on line 118 as represented by block 105 as to the particular time period, whether such is pre-meal, post-meal, bedtime, or at some miscellaneous time. Additionally, the meal type such as breakfast, lunch, dinner, or snack is inserted as represented by block 105 for insert into processor 116 for determination of the appropriate correction factors and bolus to be calculated.

System 100 provides the patient with calculated insulin dosage instructions based on nutritional and physical information, as well as personal history of insulin administration and resulting blood glucose levels as previously described. The calculated insulin dosage instructions are output to the subject on subject data display 110 which can be the monitor of a PC or through some other type of audio or sensory indication to the subject. The resulting data is then inserted into remote processor 114 for storage of the data where prior basal dosages, prior blood glucose doses, hypoglycemia thresholds, subject insulin sensitivity factor, whether a meal plan is in effect, and mid-point of target ranges are maintained in storage.

Once the user has manually input the current glucometer reading of his/her blood glucose level from block 102 along with the time period and meal type as represented in block 105, the subject further includes input as to a physical condition from block 101. All of this data is then inserted into processor 116 where the physical condition is initially calculated independent of the further processing to be accomplished by processor 116. The physical condition may require administration of a predetermined amount of carbohydrates as calculated in FIG. 3 for each time period of exercise which has been accomplished or is being planned and such is inserted into subject data display 110. Prior basal dosages and prior BG doses of the subject for previous time periods of pre-meal, post-meal, bedtime, or miscellaneous as well as prior BG doses associated with specific time periods and meal types is stored in remote processor 114 along with the hypoglycemia threshold and the mid-point of the target range ($T_m$). All of this is inserted into processor 116 on line 124 for calculations in blocks 104 and 108.

System 100 then processes all data drawing on the preset conditions and subject history for determining optimum dosage levels of the subject's current condition where all calculated data is then displayed as represented by block 110 and the calculated data is then stored in remote processor 114.

FIG. 2 is representative of the calculation blocks 104 and 108 in a further breakdown of the processor calculation procedures. The system 100 processes patient input of dietary events in FIG. 2 where initially the subject indicates whether the current blood glucose level read from glucometer reading 102 is a time period of a pre-meal (decision block 202), post-meal (decision block 230), prior to bedtime (decision block 248), or mid-sleep cycle (decision block 250). If the time period is neither pre-meal, post-meal, bedtime, or during the mid-sleep cycle, then the time period is miscellaneous as represented by input block 252. Thus, all time periods are then represented and appropriate calculations can be processed. Each of the decision blocks 202, 204, 206, 208, 210 or 203, 232, 234, 236, 238, or 248 and 250 define individual series of decision blocks. A positive indication for one decision block implies a negative indication for other decision blocks in each series. This type of event oriented organization permits the subject to expeditiously enter important information.

If the time period is pre-meal as determined in decision block 202, the patient elects or indicates whether the pre-meal reading is breakfast as shown in decision block 204. As previously described, if the pre-meal is not breakfast, the election is made for lunch in decision block 206, dinner in block 208, or a snack in decision block 210. An algorithm within processor 116 calculates the dosage correction for the planned meal using the calculation algorithm as previously described in FIG. 4 in association with sub-algorithms provided in FIGS. 5-7 and in overall block diagram shown in blocks 212, 214, 216, and 218 of FIG. 2.

In the time period of pre-meal and breakfast, the basal dose is adjusted as indicated in block 220 in association with the logic flow shown in FIG. 6.

For all pre-meals such as breakfast, lunch, dinner, snack, or miscellaneous, the pre-meal bolus or recommended insulin dosage is calculated in associated blocks 228, 222, 224, and 226. If the meal type is neither breakfast, lunch, dinner, or a snack, then it is defined as a miscellaneous time period and the calculations for the bolus are input into block 252 and the calculated correction is made in block 258 as previously detailed. All recommended optimum doses to be taken in any of the time periods is then displayed to the subject on display 110 and the data inserted into remote processor 114 for further use for subsequent blood glucose readings at specific meal types and time periods.

Mealtime nutritional information may be input by the subject and a post-meal bolus correction is calculated for correcting unacceptable blood glucose levels within the logic of processor 136 as indicated by block 108 in FIG. 1 in association with FIG. 5 logic.

In the event that the time period of the blood glucose reading is post-meal and determined in decision block 230, once again the meal type is determined from the decision blocks 232, 234, 236, or 238 for respective calculation of the post-meal type correction in respective blocks 240, 242, 244, and 246. Each of the decision blocks 230, 232, 234, 236, and 238 determine a series of decision blocks where a positive indication for one decision block defines a negative indication for other decision blocks in this series.

As shown in FIG. 2, if the time period is bedtime as determined in decision block 248, a pre-sleep blood glucose correction dose is calculated in calculation block 254 associated with calculations performed in the logic steps as provided in FIG. 4. In the event that the blood glucose reading is mid-sleep as determined in decision block 250, where it has been determined in decision block 248 that the time period is not bedtime, the logic blows into decision block 250 where it is determined whether the time period is mid-sleep and if the time period is mid-sleep, calculations are made in block 256 in accordance with the logic flow in FIG. 4. All information is then inserted on line 286 for insert into subject display 110 and remote processor 114.

In the event that one of the meal types previously discussed are found for either the pre-meal, post-meal, mid-sleep or bedtime calculations, the meal type is defaulted to input block 252 where it is determined that the meal type is miscellaneous and then passes to calculation block 258 for calculation in accordance with the calculations processed in FIG. 4. Once again, the information from block 258 is inserted onto line 286 for display and storage of the data in respective blocks 110 and 114. As previously discussed, if the information exiting decision blocks 210 and 238 indicate that the meal type was neither breakfast, lunch, dinner, or a snack, the information is directed to input block 252 and then inserted into block 258 for calculation in accordance with the logic associated with FIG. 4.

FIG. 4 is a sub-system which takes information from FIG. 2 and is associated with the calculation blocks 212, 214, 216, and 218 for the pre-meal blood glucose reading time period, as well as logic blocks 240, 242, 244, and 246 for the post-meal time period and blocks 254, 256, and 258 for the time periods of bedtime, mid-sleep or miscellaneous. The calculation blocks of FIG. 2 are read into decision block 402 for determination of whether insulin has been administered within a predetermined time interval of the taking of the blood glucose reading and if insulin has been given within this predetermined time, there is no correction dosage recommended by system 100 and the information is returned to FIG. 2 for further processing.

If the insulin has not been given within the predetermined period of time (which is generally two hours), it is determined in decision block 412 whether the subject's blood glucose level is below a pre-set hypoglycemia risk level ($H_1$) (hypoglycemia threshold). If it is not below the $H_1$, information then is directed to decision block 404 where it is determined whether the blood glucose reading is greater than the mid-point of the target range and if it is not, information is then sent back to block 408 where no correction dose is recommended and the system returns to FIG. 2.

If the blood glucose reading is greater than the mid-point of the target range as determined in decision block 404, the information then is directed to block 410 where a correction dosage is calculated as previously discussed in relation to the correction dosage equation. The correction dosage is then inserted into decision block 480 where it is determined whether the time period is pre-meal and whether the meal type is breakfast. If the data corresponds to both of these two criteria, the information is then inserted into FIG. 6 for calculation of the recommended basal dose based upon previous mid-sleep blood glucose levels and adjustment factors in FIG. 7. The logic then flows on line 486 to FIG. 5 as shown by transfer block 488. If the information does not correspond to both a breakfast and pre-meal time period in decision block 420, the information then goes directly to FIG. 5 for further calculations as previously discussed.

In overall concept, if the decision in decision block 412 determines that the blood glucose level is below $H_1$, the system requests input in decision block 414 regarding the consciousness of the subject. If consciousness is not impaired, the data then flows to block 420 for administration of a predetermined amount of oral glucose (generally 15 grams). If the subject does have impaired consciousness, the physician or caregiver is then instructed to either administer glucogen in block 420 or if there is IV access, for intravenous insertion of an insulin based upon a 50% saline solution and insulin in accordance with the previously defined equations.

Sub-system 500 shown in FIG. 5 illustrates the logic flow within processor 116 associated with adjustment factors calculated in sub-system 700 shown in FIG. 7 which are incorporated into the meal time bolus calculations in the respective calculation blocks 228, 222, 224, and 226 of FIG. 2. For respective meal types, calculation adjustment factors are calculated in the logic flow of FIG. 7 and then the current bolus is calculated as a function of the previous meal type bolus times the adjustment factor for each of the meal types in respective blocks 518, 520, 522, and 524 as well as a determination of whether the subject is on a meal plan. Information is then sent to subject display 110 and remote processor 114 subsequent to the calculations made.

Sub-system 600 shown in FIG. 6 describes the system 100 processing for incorporating the patient's personal fasting glucose levels into the adjustment factor (FIG. 7) for an increased defective recommended basal dose. A determination is made if it is determined that this is a breakfast and pre-meal meal type and time period in FIG. 4, the information is sent to block 422 where it then is transmitted on line 424 to the decision block 426 to determine whether a mid-sleep glucose level has been taken and in decision block 426 and if it has not, such returns to FIG. 2 for calculation of the breakfast bolus in calculation block 228. If the mid-sleep glucose level has been taken, the adjustment factor it is determined whether the previous mid-sleep blood glucose level is less than the previous breakfast blood glucose level in decision block 602 and if it is then the adjustment factor is calculated in block 604 from the adjustment factors in FIG. 7. If the previous mid-sleep blood glucose level is equal to or greater than the previous breakfast blood glucose level, then the adjustment factor is calculated from FIG. 7 in block 606 and in this case, the adjustment factor is calculated using the previous breakfast blood glucose level. In either cases, information flows from either block 604 or 606 into block 608 on respective lines 632, and 634 for calculation of the new basal dosage being the previous basal dose multiplied by the adjustment factor. Once again, the recommended basal dose at a particular time period is then provided in data block 610 which is then again sent to the subject display 110 and remote processor 114 as well as back to insertion into the system in FIG. 5.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A computer-implemented method when executed on data processing hardware causes the data processing hardware to perform operations comprising:
receiving a current glucose measurement of a patient;
obtaining a glucose time period associated with a time of measuring the current glucose measurement;
determining the glucose time period of the current glucose measurement is within a pre-meal time period before the patient consumes food or other nutrients;
determining a meal type associated with the pre-meal time period of the glucose time period is breakfast;
retrieving a previous day basal dose that was administered to the patient, a previous mid-sleep glucose measurement of the patient, and a previous breakfast glucose measurement of the patient from memory hardware;
determining the lesser one of the previous mid-sleep glucose measurement or the previous breakfast glucose measurement is within one of multiple pre-configured ranges of values;
setting an adjustment factor to a preconfigured adjustment factor associated with the pre-configured range of values that includes the lesser one of the previous mid-sleep glucose measurement or the previous breakfast glucose measurement;
calculating a new basal dose of insulin for the patient by multiplying the previous day basal dose times the adjustment factor;
retrieving a configured time interval for administering the calculated new basal dose of insulin to the patient from the memory hardware; and
administering the calculated new basal dose of insulin to the patient by transmitting the calculated new basal dose of insulin to a dose administering system having a patient display at the configured time interval, the patient display configured to display the calculated new basal dose of insulin and trigger administration of the calculated new basal dose of insulin to the patient.

2. The method of claim 1, wherein the operations further comprise:
retrieving a target glucose range for the patient from the memory hardware;
comparing the current glucose measurement to a mid-point of the target glucose range greater than the hypoglycemia threshold; and
determining the current glucose measurement is greater than the mid-point of the target glucose range;
retrieving an insulin sensitivity factor for the patient from the memory hardware;
calculating a correction dose of insulin based on the current glucose measurement, the mid-point of the target glucose range, and the insulin sensitivity factor; and
administering the calculated correction dose of insulin to the patient by transmitting the calculated correction dose to the dose administering system having the patient display configured to display the calculated correction dose of insulin and trigger administration of the calculated correction dose of insulin to the patient.

3. The method of claim 2, wherein the correction dose of insulin is calculated as:

$$CD = \frac{(BG - T_m)}{(1700((T_m - 60) \times S_1 \times 24))}$$

wherein CD is the correction dose of insulin, BG is the current glucose measurement, $T_m$ is the mid-point of the target glucose range, and $S_1$ is the insulin sensitivity factor.

4. The method of claim 1, wherein the operations further comprise:
retrieving a hypoglycemia threshold from the memory hardware;
comparing the current glucose measurement to the hypoglycemia threshold; and determining the current glucose measurement is less than the hypoglycemia threshold; and determining one of:
- a recommend dosage of oral glucose for oral ingestion by the patient;
- a recommended dosage of glucagon for administration to the patient; or
- a recommended dosage of saline and insulin for intravenous insertion to the patient.

5. The method of claim 4, wherein the operations further comprise:
receiving a user input, the user input indicating that the consciousness of the patient is not impaired;
determining the recommended dosage of oral glucose for the patient to ingest; and
transmitting the recommended dosage of oral glucose to the patient display, the patient display configured to display the recommended dosage of oral glucose and trigger administration of the recommended dosage of oral glucose to the patient.

6. The method of claim 4, wherein the operations further comprise:
receiving a user input, the user input indicating that the consciousness of the patient is impaired;
determining the recommended dosage of glucagon for administration to the patient; and
transmitting the recommended dosage of glucagon to the patient display, the patient display configured to display the recommended dosage of glucagon and trigger administration of the recommended dosage of glucagon to the patient.

7. The method of claim 4, wherein the operations further comprise:
receiving a user input, the user input indicating that the consciousness of the patient is impaired;
determining the recommended dosage of saline and insulin for intravenous insertion to the patient; and
transmitting the recommended dosage of saline and insulin to the patient display, the patient display configured to display the recommended dosage of saline and insulin and trigger administration of the recommended dosage of saline and insulin to the patient.

8. The method of claim 1, wherein the operations further comprise:
calculating a meal bolus for the patient; and
administering the calculated meal bolus to the patient by transmitting the calculated meal bolus to the dose administering system having the patient display, the patient display configured to display the calculated meal bolus and trigger administration of the calculated meal bolus to the patient.

9. The method of claim 1, wherein the operations further comprise:
retrieving a previous meal bolus administered by the patient for the associated meal type from the memory hardware;
determining the current glucose measurement is within one of multiple pre-configured ranges of values;
setting a meal bolus adjustment factor to a preconfigured meal bolus adjustment factor associated with the pre-configured range of values that includes the current glucose measurement;
calculating a current meal bolus for the patient based on the meal bolus adjustment factor and the previous meal bolus; and
administering the calculated current meal bolus to the patient by transmitting the calculated current meal bolus to the dose administering system having the patient display, the patient display configured to display the calculated current meal bolus and trigger administration of the calculated current meal bolus to the patient.

10. The method of claim 9, wherein calculating the current meal bolus comprises:
when the patient is on a fixed meal plan, calculating the current meal bolus by multiplying the previous meal bolus times the meal bolus adjustment factor; or
when the patient is not on a fixed meal plan:
- receiving an estimated number of carbohydrates to be ingested by the patient for the associated meal type from the user interface;
- obtaining a current carbohydrate to insulin ratio for the associated meal type; and
- calculating the current meal bolus by dividing the estimated number of carbohydrates by the current carbohydrate to insulin ratio for the associated meal type.

11. The method of claim 10, wherein obtaining the current carbohydrate to insulin ratio for the associated meal type comprises:
retrieving a previous carbohydrate to insulin ratio for the associated meal type from the memory hardware, the previous carbohydrate to insulin ratio associated with the previous meal bolus; and
calculating the current carbohydrate to insulin ratio for the associated meal type by dividing the previous carbohydrate to insulin ratio by the meal bolus adjustment factor.

12. The method of claim 11, wherein the previous carbohydrate to insulin ratio for the associated meal type is calculated as:

$$CIR_{P_{B,L,D,S}} = 450 \times TDD_M \times \omega_s$$

wherein $CIR_{P_{B,L,D,S}}$ is the previous carbohydrate to insulin ratio for the associated meal type, $TDD_m$ is a total daily dose of insulin multiplier, and $\omega_s$ is a weight of the patient.

13. The method of claim 1, wherein the operations further comprise:
receiving a user input indicating the patient plans to exercise or has recently exercised;
retrieving a target glucose range for the patient from the memory hardware; and
determining the current glucose measurement is less than a mid-point of the target glucose range;
determining a duration of the exercise planned by the patient or recently completed by the patient;
determining carbohydrate intake instructions for the patient including a predetermined amount of carbohydrates for the patient to ingest based on the duration of the exercise; and
transmitting the carbohydrate intake instructions to the patient display, the patient display configured to display the carbohydrate intake instructions.

14. (Rejoined) A system comprising:
a glucose measuring device measuring glucose measurements of a patient;
memory hardware; and
data processing hardware in communication with the glucose measuring device and the memory hardware, the data processing processor performing operations comprising:
receiving a current glucose measurement from the glucose measuring device;

obtaining a glucose time period associated with a time of measuring the current glucose measurement;

determining whether the glucose time period of the current glucose measurement is within a pre-meal time period before the patient consumes food or other nutrients;

when the glucose time period of the current glucose measurement is within the pre-meal time, determining whether a meal type associated with the pre-meal time period of the glucose time period is one of breakfast, lunch, dinner, or snack; and when the meal type associated with the pre-meal time period of the glucose time period is breakfast:
retrieving a previous day basal dose that was administered to the patient, a previous mid-sleep glucose measurement of the patient, and a previous breakfast glucose measurement of the patient from the memory hardware;
determining whether the lesser one of the previous mid-sleep glucose measurement or the previous breakfast glucose measurement is within one of multiple pre-configured ranges of values;
setting an adjustment factor to a preconfigured adjustment factor associated with the pre-configured range of values that includes the lesser one of the previous mid-sleep glucose measurement or the previous breakfast glucose measurement;
calculating a new basal dose for the patient by multiplying the previous day basal dose times the adjustment factor;
retrieving a configured time interval for administering the calculated new basal dose to the patient from the memory hardware, the configured time interval input to the memory hardware by the data processing processor; and
administering the calculated new basal dose to patient by transmitting the calculated new basal dose to a dose administering system having a patient display at the configured time interval, the patient display configured to display the calculated new basal dose and trigger administration of the calculated new basal dose to the patient.

15. The system of claim 14, wherein the operations further comprise:
retrieving a target glucose range for the patient from the memory hardware;
comparing the current glucose measurement to a mid-point of the target glucose range greater than the hypoglycemia threshold; and
when the current glucose measurement is greater than the mid-point of the target glucose range:
retrieving an insulin sensitivity factor for the patient from the memory hardware;
calculating a correction dose based on a function of the current glucose measurement, the mid-point of the target glucose range, and the insulin sensitivity factor; and
administering the calculated correction dose to the patient by transmitting the calculated correction dose to the dose administering system having the patient display, the patient display configured to display the calculated correction dose and trigger administration of the calculated correction dose to the patient.

16. The system of claim 15, wherein the operations further comprise, when the glucose time period is not within the pre-meal time period, calculating the correction dose based on the function of the current glucose measurement, the mid-point of the target glucose range, and the insulin sensitivity factor.

17. The system of claim 15, wherein the correction dose is calculated as:

$$CD = \frac{(BG - T_m)}{(1700((T_m - 60) \times S_1 \times 24))}$$

wherein CD is the correction dose, BG is the current glucose measurement, $T_m$ is the mid-point of the target glucose range, and $S_1$ is the insulin sensitivity factor.

18. The system of claim 14, wherein the operations further comprise:
retrieving a hypoglycemia threshold from the memory hardware;
comparing the current glucose measurement to the hypoglycemia threshold; and
when the current glucose measurement is less than the hypoglycemia threshold, determining one of:
a recommend dosage of oral glucose for oral ingestion by the patient;
a recommended dosage of glucagon for administration to the patient; or
a recommended dosage of saline and insulin for intravenous insertion to the patient.

19. The system of claim 18, wherein the operations further comprise, when the current glucose measurement is less than the hypoglycemia threshold:
requesting a user input indicating whether the consciousness of the patient is impaired;
when the user input indicates that the consciousness of the patient is not impaired, determining the recommended dosage of oral glucose for the patient to ingest; and
transmitting the recommended dosage of oral glucose to the patient display, the patient display configured to display the recommended dosage of oral glucose and trigger administration of the recommended dosage of oral glucose to the patient.

20. The system of claim 18, wherein the operations further comprise, when the current glucose measurement is less than the hypoglycemia threshold:
requesting a user input indicating whether the consciousness of the patient is impaired;
when the user input indicates that the consciousness of the patient is impaired, determining the recommended dosage of glucagon for administration to the patient; and
transmitting the recommended dosage of glucagon to the patient display, the patient display configured to display the recommended dosage of glucagon and trigger administration of the recommended dosage of glucagon to the patient.

21. The system of claim 18, wherein the operations further comprise, when the current glucose measurement is less than the hypoglycemia threshold:
requesting a user input indicating whether the consciousness of the patient is impaired;
when the user input indicates that the consciousness of the patient is impaired, determining the recommended dosage of saline and insulin for intravenous insertion to the patient; and
transmitting the recommended dosage of saline and insulin to the patient display, the patient display configured to display the recommended dosage of saline and insulin and trigger administration of the recommended dosage of saline and insulin to the patient.

22. The system of claim 14, wherein the operations further comprise, when the glucose time period of the current glucose measurement is the pre-meal time and the meal type associated with the pre-meal time is one of breakfast, lunch, dinner or snack:
   calculating a meal bolus for the patient; and
   administering the calculated meal bolus to the patient by transmitting the calculated meal bolus to the dose administering system having the patient display, the patient display configured to display the calculated meal bolus and trigger administration of the calculated meal bolus to the patient.

23. The system of claim 14, wherein the operations further comprise, when the glucose time period of the current glucose measurement is the pre-meal time and the meal type associated with the pre-meal time is one of breakfast, lunch, dinner or snack:
   retrieving a previous meal bolus administered by the patient for the associated meal type from the memory hardware;
   determining the current glucose measurement is within one of multiple pre-configured ranges of values;
   setting a meal bolus adjustment factor to a preconfigured meal bolus adjustment factor associated with the pre-configured range of values that includes the current glucose measurement;
   calculating a current meal bolus for the patient based on the meal bolus adjustment factor and the previous meal bolus; and
   administering the calculated current meal bolus to the patient by transmitting the calculated current meal bolus to the dose administering system having the patient display, the patient display configured to display the calculated current meal bolus and trigger administration of the calculated current meal bolus to the patient.

24. The system of claim 23, wherein calculating the current meal bolus comprises:
   when the patient is on a fixed meal plan, calculating the current meal bolus by multiplying the previous meal bolus times the meal bolus adjustment factor; or
   when the patient is not on a fixed meal plan:
      receiving an estimated number of carbohydrates to be ingested by the patient for the associated meal type from the user interface;
      obtaining a current carbohydrate to insulin ratio for the associated meal type; and
      calculating the current meal bolus by dividing the estimated number of carbohydrates by the current carbohydrate to insulin ratio for the associated meal type.

25. The system of claim 24, wherein obtaining the current carbohydrate to insulin ratio for the associated meal type comprises:
   retrieving a previous carbohydrate to insulin ratio for the associated meal type from the memory hardware, the previous carbohydrate to insulin ratio associated with the previous meal bolus; and
   calculating the current carbohydrate to insulin ratio for the associated meal type by dividing the previous carbohydrate to insulin ratio by the meal bolus adjustment factor.

26. The system of claim 25, wherein the previous carbohydrate to insulin ratio for the associated meal type is calculated as:

$$CIR_{P_{B,L,D,S}} = 450 \times TDD_M \times \omega_s$$

wherein $CIR_{P_{B,L,D,S}}$ is the previous carbohydrate to insulin ratio for the associated meal type, $TDD_M$ is a total daily dose of insulin multiplier, and $\omega_s$ is a weight of the patient.

27. The system of claim 14, wherein the operations further comprise:
   receiving a user input indicating the patient plans to exercise or has recently exercised;
   retrieving a target glucose range for the patient from the memory hardware; and
   when the current glucose measurement is less than a mid-point of the target glucose range:
      determining a duration of the exercise planned by the patient or recently completed by the patient;
      determining carbohydrate intake instructions for the patient including a predetermined amount of carbohydrates for the patient to ingest based on the duration of the exercise; and
      transmitting the carbohydrate intake instructions to the patient display, the patient display configured to display the carbohydrate intake instructions.

* * * * *